(12) United States Patent
Demuth et al.

(10) Patent No.: US 12,138,301 B2
(45) Date of Patent: Nov. 12, 2024

(54) COMPOUNDS INCLUDING A MUTANT KRAS SEQUENCE AND A LIPID AND USES THEREOF

(71) Applicant: Elicio Therapeutics, Inc., Cambridge, MA (US)

(72) Inventors: Peter C. Demuth, Medford, MA (US); Julian Adams, Boston, MA (US); Martin Steinbuck, Boston, MA (US)

(73) Assignee: Elicio Therapeutics, Inc., Boston, MA (US)

( * ) Notice: Subject to any disclaimer, the term of this patent is extended or adjusted under 35 U.S.C. 154(b) by 1077 days.

(21) Appl. No.: 16/977,155

(22) PCT Filed: Mar. 1, 2019

(86) PCT No.: PCT/US2019/020404
§ 371 (c)(1),
(2) Date: Sep. 1, 2020

(87) PCT Pub. No.: WO2019/169332
PCT Pub. Date: Sep. 6, 2019

(65) Prior Publication Data
US 2021/0060149 A1    Mar. 4, 2021

Related U.S. Application Data

(60) Provisional application No. 62/637,879, filed on Mar. 2, 2018.

(51) Int. Cl.
| | | |
|---|---|---|
| A61K 39/00 | (2006.01) | |
| A61K 39/39 | (2006.01) | |
| A61K 47/54 | (2017.01) | |
| A61K 47/60 | (2017.01) | |
| A61P 35/00 | (2006.01) | |
| C07K 7/00 | (2006.01) | |
| C12N 9/14 | (2006.01) | |
| C12N 9/96 | (2006.01) | |

(52) U.S. Cl.
CPC ...... *A61K 39/001164* (2018.08); *A61K 39/39* (2013.01); *A61K 47/543* (2017.08); *A61K 47/60* (2017.08); *A61P 35/00* (2018.01); *C12N 9/14* (2013.01); *C12N 9/96* (2013.01); *C12Y 306/05002* (2013.01); *A61K 2039/545* (2013.01); *A61K 2039/55561* (2013.01)

(58) Field of Classification Search
CPC .......... A61K 39/001164; A61K 47/543; C12N 9/14; C07K 7/00
See application file for complete search history.

(56) References Cited

U.S. PATENT DOCUMENTS

| | | |
|---|---|---|
| 5,961,978 A * | 10/1999 | Gaudernack ............ A61P 37/04 424/277.1 |
| 6,168,778 B1 | 1/2001 | Janjic et al. |
| 7,709,002 B1 | 5/2010 | Schlom et al. |
| 9,107,904 B2 | 8/2015 | Irvine et al. |
| 10,029,016 B2 | 7/2018 | Irvine et al. |
| 10,940,201 B2 | 3/2021 | Kugimiya et al. |
| 10,953,105 B2 | 3/2021 | Irvine et al. |
| 2007/0298449 A1 | 12/2007 | Saito et al. |
| 2008/0299138 A1 | 12/2008 | Duffy et al. |
| 2010/0074945 A1 | 3/2010 | Schlom et al. |
| 2012/0264810 A1 | 10/2012 | Lin et al. |
| 2012/0328701 A1 | 12/2012 | Edelson et al. |
| 2014/0044755 A1 | 2/2014 | Naoi et al. |
| 2016/0220669 A1 | 8/2016 | Hoves et al. |
| 2016/0264810 A1 | 9/2016 | Okamoto et al. |
| 2017/0246288 A1 | 8/2017 | Li et al. |
| 2019/0048049 A1 | 2/2019 | Dasseux |
| 2020/0061172 A1 | 2/2020 | Kulangara et al. |
| 2021/0040159 A1 | 2/2021 | DeMuth et al. |
| 2021/0060149 A1 | 3/2021 | DeMuth et al. |

FOREIGN PATENT DOCUMENTS

| | | |
|---|---|---|
| CN | 1902311 A | 1/2007 |
| CN | 101265285 A | 9/2008 |
| CN | 104685055 A | 6/2015 |

(Continued)

OTHER PUBLICATIONS

Wang et al., 2012, Application of poly(ethylene glycol)-distearoylphosphatidylethanolamine (PEG-DSPE) block copolymers and their derivatives as nanomaterials in drug delivery, International Journal of Nanomedicine, 7: 4185-4198.*
Lu et al, "Structural dataset for the fast-exchanging KRAS G13D," Data Brief. 5:572-578 (Oct. 2015).
Notice of Reasons for Refusal for Japanese Patent Application No. 2020-568946 dated Feb. 14, 2023 (8 pages).
Office Action for Chinese Patent Application No. 201980028790.5, dated Mar. 21, 2023 (18 pages).

(Continued)

*Primary Examiner* — Amber D Steele
(74) *Attorney, Agent, or Firm* — Clark & Elbing LLP

(57) ABSTRACT

The invention features a compound including a mutant KRAS sequence and a lipid, where the mutant KRAS sequence is conjugated to the lipid by a linker, and (i) the linker includes one or more polyethylene glycol blocks, (ii) the lipid is 1,2-distearoyl-sn-glycero-3-phosphoethanolamine (DSPE), and (iii) the mutant KRAS sequence comprises or consists of the amino acid sequence selected from the group consisting of SEQ ID NOs:1-7 and 22-30. The invention features a composition including one or more compounds of the invention and a pharmaceutically acceptable carrier. The invention also features a method of treating a cancer in a human patient, the method including administering the composition to the patient. Further, the invention features a kit comprising the compound.

34 Claims, 7 Drawing Sheets

Specification includes a Sequence Listing.

(56) References Cited

FOREIGN PATENT DOCUMENTS

| JP | 2008-500275 A | 1/2008 |
|---|---|---|
| WO | WO-98/18810 A1 | 5/1998 |
| WO | WO-2005/065239 A2 | 7/2005 |
| WO | WO-2013/151771 A1 | 10/2013 |
| WO | WO-2016/040887 A2 | 3/2016 |
| WO | WO-2017/127473 A1 | 7/2017 |
| WO | WO-2018/102584 A1 | 6/2018 |
| WO | WO-2019/169332 A1 | 9/2019 |

OTHER PUBLICATIONS

Pan et al., "Immunoprevention of KRAS-driven lung adenocarcinoma by a multipeptide vaccine," Oncotarget. 8(47):82689-82699 (Aug. 2017).
Wang et al., "In vitro and in vivo evaluations of human papillomavirus type 16 (HPV16)-derived peptide-loaded dendritic cells (DCs) with a CpG oligodeoxynucleotide (CpG-ODN) adjuvant as tumor vaccines for immunotherapy of cervical cancer," Arch Gynecol Obstet. 289(1):155-62 (Epub Aug. 2013).
New Compilation of Clinical Medical Technology. Ping Wei/ Yunnan Science and Technology Press, 218 (Jun. 2014) (4 pages).
Yu et al., "Immunostimulatory Properties of Lipid Modified CpG Oligonucleotides," Mol Pharm. 14(8):2815-2823 (2017).
Extended European Search Report for European Patent Application No. 19761691.5 dated Nov. 26, 2021 (9 pages).
Written Opinion for Singaporean Application No. 11202008433Q dated Feb. 21, 2022 (7 pages).
International Preliminary Report on Patentability for International Patent Application No. PCT/US2019/020398, dated Sep. 8, 2020 (6 pages).
International Preliminary Report on Patentability for International Patent Application No. PCT/2019/020404 dated Sep. 8, 2020 (4 pages).
International Search Report for International Patent Application No. PCT/US2019/020398, dated Jun. 13, 2019 (4 pages).
International Search Report for International Patent Application No. PCT/2019/020404 dated Jun. 24, 2019 (4 pages).
Liu et al., "Structure-based programming of lymph-node targeting in molecular vaccines," Nature. 507(7493):519-22 (2014) (15 pages).
Non-Final Office Action for U.S. Appl. No. 16/977,185, dated Aug. 9, 2021 (12 pages).
Written Opinion of the International Searching Authority for International Patent Application No. PCT/US2019/020398, dated Jun. 13, 2019 (5 pages).
Written Opinion of the International Searching Authority for International Patent Application No. PCT/2019/020404 dated Jun. 24, 2019 (3 pages).
Official Action and Search Report with English Translation for Russian Application No. 2020132290, dated Sep. 2, 2022 (15 pages).
An, Xu, Thesis: "The Role and Mechanism of Oncogene Kras in Nonalcoholic Fatty Liver Disease and Its Transition to Hepatocellular Carcinoma," Ph.D., Second Military Medical University 1-92 (2017). English abstract retrieved from <https://kns.cnki.net/KCMS/detail/detail.aspx?dbname=CDFDLAST2017&filename=1017208382. n h> (4 pages).
Cogoi et al., "Lipid-modified G4-decoy oligonucleotide anchored to nanoparticles: delivery and bioactivity in pancreatic cancer cells," Sci Rep. 6:38468 (Dec. 2016) (13 pages).
Office Action for Chinese Patent Application No. 201980028790.5 issued Nov. 20, 2023 (24 pages).

* cited by examiner

COMPOUNDS INCLUDING A MUTANT KRAS SEQUENCE AND A LIPID AND USES THEREOF

SEQUENCE LISTING

The instant application contains a Sequence Listing which has been submitted electronically in ASCII format and is hereby incorporated by reference in its entirety. Said ASCII copy, created on Aug. 26, 2020 is named 51026-026002_Sequence_Listing_8.26.20 and is 7,899 bytes in size.

BACKGROUND OF THE INVENTION

RAS proteins are essential components of cell signaling pathways. Oncogenic activation of RAS proteins by mutation is frequently detected in several types of cancer, including pancreatic cancer. There continues to be a need for further and more effective cancer treatments.

SUMMARY OF THE INVENTION

The invention provides compounds that can be used in therapeutic methods.

Accordingly, in the first aspect, the invention features a compound including a mutant KRAS sequence and a lipid, where the mutant KRAS sequence is conjugated to the lipid by a linker, and (i) the linker includes one or more polyethylene glycol blocks, (ii) the lipid is 1,2-distearoyl-sn-glycero-3-phosphoethanolamine (DSPE), and (iii) the mutant KRAS sequence comprises or consists of an amino acid sequence selected from the group consisting of YKLVVVGADGVGKSALTI (SEQ ID NO:23), YKLVVVGAVGVGKSALTI (SEQ ID NO:24), YKLVVVGARGVGKSALTI (SEQ ID NO:25), YKLVVVGAAGVGKSALTI (SEQ ID NO:26), YKLVVV-GASGVGKSALTI (SEQ ID NO:27), YKLVVVGACGVGKSALTI (SEQ ID NO:28), YKLVW-GATGVGKSALTI (SEQ ID NO:29), and YKLVVVGAGDVGKSALTI (SEQ ID NO:30).

In the second aspect, the invention features a compound including a mutant KRAS sequence and a lipid, where the mutant KRAS sequence is conjugated to the lipid by a linker, and (i) the linker includes one or more polyethylene glycol blocks, (ii) the lipid is 1,2-distearoyl-sn-glycero-3-phosphoethanolamine (DSPE), and (iii) the mutant KRAS sequence comprises or consists of an amino acid sequence selected from the group consisting of CYKLVVVGADGVGKSALTI (SEQ ID NO:1), CYKLVVVGAVGVGKSALTI (SEQ ID NO:2), CYKLWVGARGVGKSALTI (SEQ ID NO:3), CYKLVVVGAAGVGKSALTI (SEQ ID NO:4), CYKLVVVGASGVGKSALTI (SEQ ID NO:5), CYKLWVGACGVGKSALTI (SEQ ID NO:6), CYKLVVV-GATGVGKSALTI (SEQ ID NO:22), and CYKLVVVGAGDVGKSALTI (SEQ ID NO:7).

In one embodiment of the first and the second aspects of the invention, the mutant KRAS sequence, at its N-terminus, is conjugated to the linker through a cysteine-maleimide linkage.

In another embodiment of the first and the second aspects of the invention the linker includes 48 repeat units of polyethylene glycol.

In an additional embodiment of the first and the second aspects of the invention, the mutant KRAS sequence, at its N-terminus, is conjugated to the following structure:

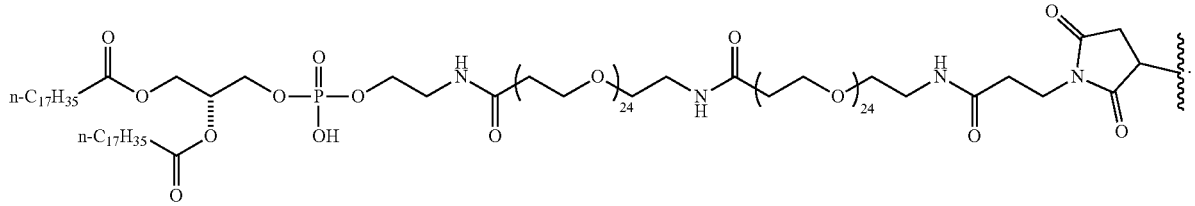

In the third aspect, the invention features a composition including one or more compounds of the first and the second aspects of the invention and a pharmaceutically acceptable carrier.

In one embodiment of the third aspect of the invention, the composition includes (1) a compound including the amino acid sequence YKLVVVGADGVGKSALTI (SEQ ID NO:23), (2) a compound including the amino acid sequence YKLWVGAVGVGKSALTI (SEQ ID NO:24), (3) a compound including the amino acid sequence YKLWVGARGVGKSALTI (SEQ ID NO:25), (4) a compound including the amino acid sequence YKLVVVGAAGVGKSALTI (SEQ ID NO:26), (5) a compound including the amino acid sequence YKLVVV-GASGVGKSALTI (SEQ ID NO:27), (6) a compound including the amino acid sequence YKLVVVGACGVGK-SALTI (SEQ ID NO:28) or a compound including the amino acid sequence YKLWVGATGVGKSALTI (SEQ ID NO:29), and (7) a compound including the amino acid sequence YKLVVVGAGDVGKSALTI (SEQ ID NO:30).

In one embodiment of the third aspect of the invention, the composition includes (1) a compound including the amino acid sequence YKLVVVGADGVGKSALTI (SEQ ID NO:23), (2) a compound including the amino acid sequence YKLWVGAVGVGKSALTI (SEQ ID NO:24), (3) a compound including the amino acid sequence YKLVVVGARGVGKSALTI (SEQ ID NO:25), (4) a compound including the amino acid sequence YKLVVVGAAGVGKSALTI (SEQ ID NO:26), (5) a compound including the amino acid sequence YKLWV-GASGVGKSALTI (SEQ ID NO:27), (6) a compound including the amino acid sequence YKLWVGACGVGK-SALTI (SEQ ID NO:28), and (7) a compound including the amino acid sequence YKLVVVGAGDVGKSALTI (SEQ ID NO:30).

In another embodiment of the third aspect of the invention, the composition includes (1) a compound including the amino acid sequence CYKLVVVGADGVGKSALTI (SEQ ID NO:1), (2) a compound including the amino acid sequence CYKLVWGAVGVGKSALTI (SEQ ID NO:2), (3) a compound including the amino acid sequence CYKLVVVGARGVGKSALTI (SEQ ID NO:3), (4) a compound including the amino acid sequence CYKLVW-GAAGVGKSALTI (SEQ ID NO:4), (5) a compound including the amino acid sequence CYKLVVVGASGVGKSALTI (SEQ ID NO:5), (6) a compound including the amino acid sequence CYKLVVVGACGVGKSALTI (SEQ ID NO:6) or a compound including the amino acid sequence CYKLVVV-GATGVGKSALTI (SEQ ID NO:22), and (7) a compound including the amino acid sequence CYKLVVVGAGDVGKSALTI (SEQ ID NO:7).

In another embodiment of the third aspect of the invention, the composition includes (1) a compound including the amino acid sequence CYKLVVVGADGVGKSALTI (SEQ ID NO:1), (2) a compound including the amino acid sequence CYKLVVVGAVGVGKSALTI (SEQ ID NO:2), (3) a compound including the amino acid sequence CYKLVVVGARGVGKSALTI (SEQ ID NO:3), (4) a compound including the amino acid sequence CYKLVVVGAAGVGKSALTI (SEQ ID NO:4), (5) a compound including the amino acid sequence CYKLVVV-GASGVGKSALTI (SEQ ID NO:5), (6) a compound including the amino acid sequence CYKLVVVGACGVGKSALTI (SEQ ID NO:6), and (7) a compound including the amino acid sequence CYKLVVVGAGDVGKSALTI (SEQ ID NO:7).

In some embodiments, 700 µg of each compound is included in the composition.

In an additional embodiment of the third aspect of the invention, the composition further includes a compound consisting of the nucleotide sequence 5'-TCGTCGTTTTGTCGTTTTGTCGTT-3' (SEQ ID NO:8), which, at its 5' end, is bonded or linked by a linker to the following lipid:

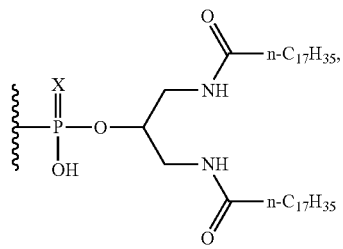

or a salt thereof, where X is O or S. In one embodiment, the nucleotide sequence is bonded to the lipid. In another embodiment, all internucleoside groups connecting the nucleosides in 5'-TCGTCGTTTTGTCGTTTTGTCGTT-3' (SEQ ID NO:8) are phosphorothioates.

In the fourth aspect, the invention features a method of treating a cancer in a human patient, the method including administering the composition of the third aspect of the invention to the patient.

In one embodiment of the fourth aspect of the invention, the method further includes administering an adjuvant, such as an adjuvant including a CpG nucleotide sequence (e.g., 5'-TCGTCGTTTTGTCGTTTTGTCGTT-3'; SEQ ID NO:8).

In some embodiments, 0.1 mg, 0.5 mg, or 2.5 mg of the adjuvant is administered.

In one embodiment of the fourth aspect of the invention, the method further includes administering to the patient a compound consisting of the nucleotide sequence 5'-TCGTCGTTTTGTCGTTTTGTCGTT-3' (SEQ ID NO:8), which, at its 5' end, is bonded or linked by a linker to the following lipid:

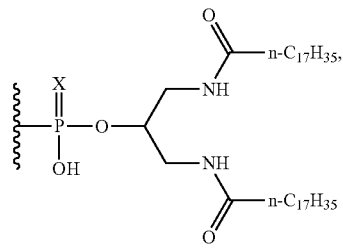

or a salt thereof, where X is O or S. In one embodiment, the nucleotide sequence is bonded to the lipid. In one embodiment, 0.1 mg, 0.5 mg, or 2.5 mg of the compound is administered.

In another embodiment, all internucleoside groups connecting the nucleosides in 5'-TCGTCGTTTTGTCGTTTTGTCGTT-3' (SEQ ID NO:8) are phosphorothioates.

In one embodiment of the fourth aspect of the invention, the cancer is a pancreatic cancer, a lung cancer, or a colorectal cancer.

In the fifth aspect, the invention features a kit including (i) a compound of any one of claims 1 to 5, or a composition of any one of claims 6-8, and (ii) a compound consisting of the nucleotide sequence 5'-TCGTCGTTTTGTCGTTTTGTCGTT-3' (SEQ ID NO:8), which, at its 5' end, is bonded or linked by a linker to the following lipid:

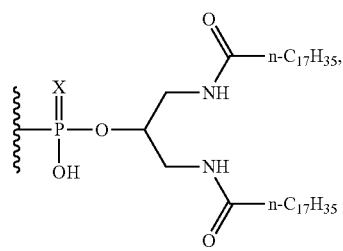

or a salt thereof, where X is O or S. In one embodiment, the nucleotide sequence is bonded to the lipid.

In another embodiment, all internucleoside groups connecting the nucleosides in 5'-TCGTCGTTTTGTCGTTTTGTCGTT-3' (SEQ ID NO:8) are phosphorothioates.

Definitions

A "carbonyl," as used herein, refers to a group —C(O)—.

A "carboxylate," as used herein, refers to a group —C(O)—OH or a salt thereof.

As used herein, "conjugated" refers to a covalent bonding of a mutant KRAS sequence to a linker and, optionally, further covalent bonding of the linker to a lipid. In various examples, the covalent bonds connecting the linker to the mutant KRAS sequence or to the lipid may be a covalent bond between a sulfur atom and a $sp^3$-hybridized carbon atom in succinimide, between a nitrogen atom and a carbon atom of a carbonyl, or between oxygen atom and the phosphorus atom of a thiophosphoryl or phosphoryl. In various examples, each of the KRAS sequence and the lipid may contain a group for bonding to a complementary group in the linker. For example, the KRAS polypeptide may include a sulfur atom (e.g., the sulfur atom in a cysteine residue) bonded to a complementary group, e.g., succinimide, in the linker. The bond from the sulfur atom in the KRAS polypeptide to the succinimide in the linker may be formed by a reaction of a thiol (e.g., a thiol in a cysteine residue) in the KRAS polypeptide and a maleimide in the linker. Alternatively, the KRAS polypeptide may include a nitrogen atom or a carbonyl group bonded to a carbonyl group or a nitrogen atom, respectively, in the linker. The bond between the carbonyl group and the nitrogen atom may be formed by a reaction between an amine or carboxylate in the KRAS polypeptide and a carboxylate or an amine, respectively, in the linker.

A "lipid" is any of a group of organic compounds that are greasy to the touch, insoluble in water, and soluble in organic solvents, and in general includes fatty acids and their derivatives. One example of a lipid used in the invention is 1,2-distearoyl-sn-glycero-3-phosphoethanolamine (DSPE).

A "linker," as used herein, refers to a monovalent or divalent group, in which one valency is covalently bonded to one biologically functional group, and the other valency is covalently bonded to another biologically functional group. In one example, a linker connects a KRAS sequence to a lipid, as noted above. Optionally, such a linker can include one or more polyethylene glycol blocks. In another example, a linker connects a nucleotide sequence of, e.g., a CpG oligonucleotide, to a lipid (e.g., —P(X)(OH)—O—CH(CH$_2$NHCO—(CH$_2$)$_{16}$—CH$_3$)$_2$, or a salt thereof, where X is O or S, as described herein). Such linkers can optionally include one or more nucleotides, for example, a dinucleotide (e.g., GG).

A "pharmaceutically acceptable carrier," as used herein, refers to a vehicle capable of suspending or dissolving an active compound, and having the properties of being non-toxic and non-inflammatory in a subject (e.g., a human patient) to whom it is administered. Moreover, a pharmaceutically acceptable carrier may include a pharmaceutically acceptable additive, such as a preservative, antioxidant, fragrance, emulsifier, dye, or excipient known or used in the field of drug formulation and that does not significantly interfere with the therapeutic effectiveness of the biological activity of the active agent, and that is non-toxic to the subject.

A "phosphoryl," as used herein, refers to a group —P(O)(OR$^A$)(OR$^B$), where R$^A$ is H, and R$^B$ is a valency.

A "polyethylene glycol," as used herein, refers to a block —(OCH$_2$CH$_2$)$_n$—, where n is a number of repeat units and is an integer from 2 to 50 (e.g., 24 or 48).

A "thiol," as used herein, refers to a group —SH.

A "thiophosphoryl," as used herein, refers to a group —P(S)(OR$^A$)(OR$^B$), where R$^A$ is H, and R$^B$ is a valency.

The terms "treat," "treatment," and "treating" refer to therapeutic approaches in which the goal is to reverse, alleviate, ameliorate, inhibit, slow down, or stop the progression or severity of a condition associated with a disease or disorder, e.g., cancer. These terms include reducing or alleviating at least one adverse effect or symptom of a condition, disease, or disorder. Treatment is generally "effective" if one or more symptoms or clinical markers are reduced, or if a desired response (e.g., a specific immune response) is induced. Alternatively, treatment is "effective" if the progression of a disease is reduced or halted.

The invention provides several advantages. For example, in including DSPE moieties, certain compounds of the invention bind to endogenous albumin in subjects to whom they are administered, which enhances delivery of the compounds to the lymph nodes of the subjects. This facilitates the induction of a therapeutic immune response against the KRAS sequences of the compounds, leading to effective cancer treatment.

Other features and advantages of the invention will be apparent from the following detailed description, the drawings, and the claims.

DETAILED DESCRIPTION OF THE INVENTION

Figure 1:
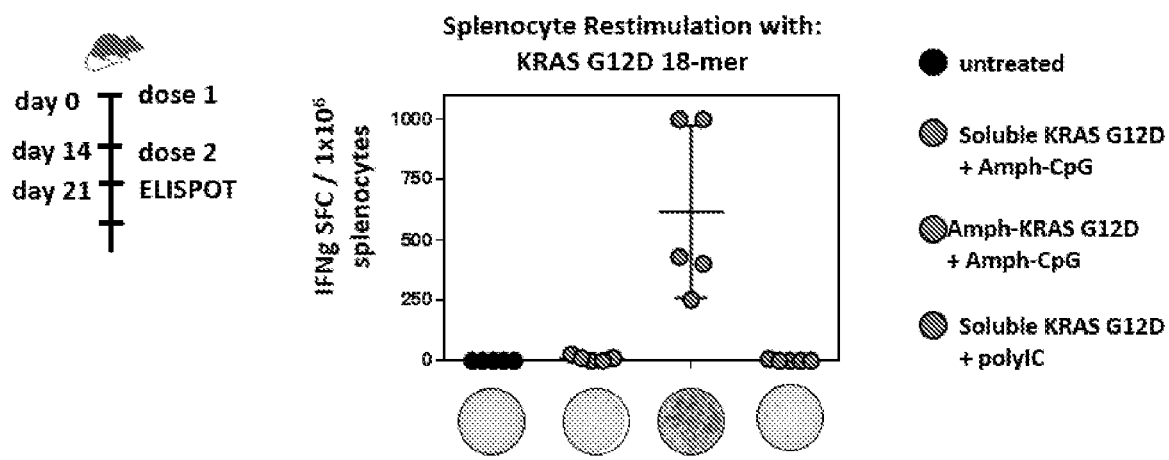
FIG. 1 shows that amphiphile-KRas (aKRas), in combination with amphiphile-CpG (aCpG), activated splenocytes, while soluble KRas, in combination with aCpG, and the untreated and soluble KRas and polyIC (pIC) control groups, did not.

The invention provides compounds that can be used in therapeutic methods. The compounds of the invention each include a mutant KRAS sequence (e.g., any one of SEQ ID NOS:1-7 and 22; see Table 1, below, or any one of SEQ ID NOS:23-30, see Table 2, below) and a lipid (e.g., 1,2-distearoyl-sn-glycero-3-phosphoethanolamine (DSPE)). These moieties (the mutant KRAS sequence and the lipid) are linked to one another by a linker, for example, a linker including one or more polyethylene glycol blocks. In one example, the linker is:

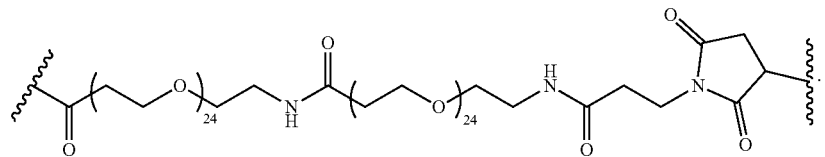

In a specific example, a mutant KRAS sequence (e.g., any one of SEQ ID NOS:1-7 or 22, or any one of SEQ ID NOS:23-30) is bonded at its N-terminus through a Cys residue to a linker, and the linker is bonded to a lipid, where the linker is:

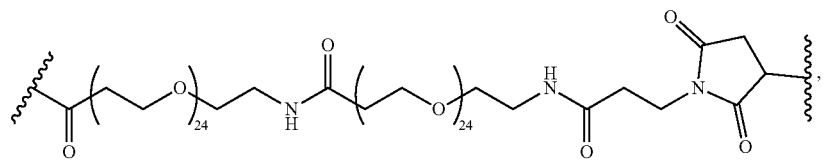

and the lipid is:

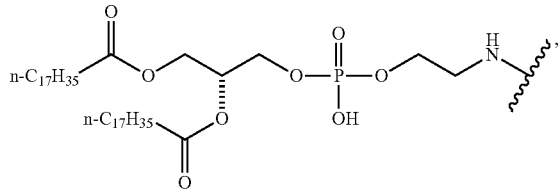

or a salt thereof.

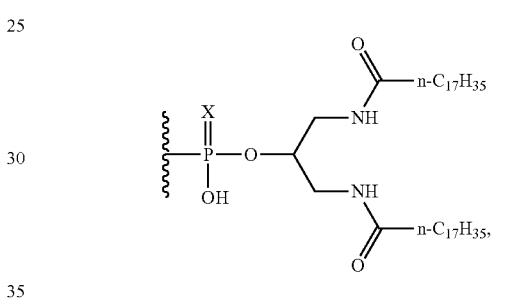

or a salt thereof, where X is O or S. Preferably, X is S.

The CpG oligonucleotide may be directly bonded to the lipid. Alternatively, the linker bonded to the CpG oligonucleotide and to the lipid may be GG. In the CpG oligonucleotide, all internucleoside groups are phosphorothioates (e.g., all internucleoside groups in the compound may be phosphorothioates).

The invention also provides compositions that include one or more compounds of the invention, together with a pharmaceutically acceptable carrier or diluent. Optionally, the compositions can include seven different compounds as described above, where each of the seven different compounds includes a different sequence selected from SEQ ID NOS:1-7 and 23 or SEQ ID NOS:23-30. Compositions including subsets (e.g., 2, 3, 4, 5, or 6) of these compounds are also included in the invention. Different compounds included in the compositions of the invention can optionally each include the same or different KRAS sequences, linkers, and/or lipids.

The compounds and compositions of the invention can be used in therapeutic methods. In particular, the KRAS sequences of the compounds can induce an immune response to KRAS, which is expressed in certain cancer cells. Accordingly, the invention provides methods of treating cancer in a subject (e.g., a human patient) by administering one or more compounds or compositions of the invention to the subject. The invention also includes methods of inducing an immune response against KRAS in a subject (e.g., a human patient) by administering one or more compounds or compositions of the invention to the subject. In various examples, the cancer is selected from the group consisting of pancreatic cancer, lung cancer, and colorectal cancer. Optionally, the methods of the invention can further include administering a compound or composition of the invention in combination with a second (or further) different approach to treatment.

The compositions of the invention can be used in methods to induce immune responses to the KRAS sequences of the compounds. Accordingly, the compositions can be referred to as immunogenic or vaccine compositions. The compositions can thus optionally include or be administered with one or more adjuvants. In one example, the adjuvant used can include a CpG oligonucleotide (e.g., 5'-TCGTCGTTTTGTCGTTTTGTCGTT-3'; SEQ ID NO:8; CpG-7909) that, at its 5' end, is bonded or linked by a linker to a lipid, such as the following:

The invention also provides kits that each contain, for example, a first vessel that includes one or more compounds of the invention, optionally together with a second vessel that includes an adjuvant, such as an adjuvant as described herein.

TABLE 1

(SEQ ID NOS: 1-7 and 22)

| Peptide | Name | Sequence | MW (Da) | Residues | Amph-Peptide MW (Da) |
|---|---|---|---|---|---|
| 1 | G12D 4-21 | CYKLVVVGADGVGKSALTI | 1893 | 19 | 5049 |
| 2 | G12V 4-21 | CYKLVVVGAVGVGKSALTI | 1877 | 19 | 5033 |
| 3 | G12R 4-21 | CYKLVVVGARGVGKSALTI | 1934 | 19 | 5090 |
| 4 | G12A 4-21 | CYKLVVVGAAGVGKSALTI | 1849 | 19 | 5005 |
| 5 | G12S 4-21 | CYKLVVVGASGVGKSALTI | 1865 | 19 | 5021 |
| 6 | G12C 4-21 or G12T 4-21 | YKLVVVGACGVGKSALTI or CYKLVVVGATGVGKSALTI | 1778 | 19 19 | 4934 |
| 7 | G13D 4-21 | CYKLVVVGAGDVGKSALTI | 1790 | 19 | 5049 |

For each of the "Amph-Peptide" referred to in Table 1, the lipid poly(ethylene glycol) moiety was conjugated via a maleimide (MAL)-cysteine coupling to the peptide using the following synthon:
DSPE-amido-dPEG24-amido-dPEG24-MAL

TABLE 2

(SEQ ID NOS: 23-30)

| Peptide | Name | Sequence | MW (Da) | Residues |
|---|---|---|---|---|
| 1 | G12D 4-21 | YKLVVVGADGVGKSALTI | 1790 | 18 |
| 2 | G12V 4-21 | YKLVVVGAVGVGKSALTI | 1774 | 18 |
| 3 | G12R 4-21 | YKLVVVGARGVGKSALTI | 1831 | 18 |
| 4 | G12A 4-21 | YKLVVVGAAGVGKSALTI | 1746 | 18 |

TABLE 2-continued

(SEQ ID NOS: 23-30)

| Peptide | Name | Sequence | MW (Da) | Residues |
|---|---|---|---|---|
| 5 | G12S 4-21 | YKLVVVGASGVGKSALTI | 1762 | 18 |
| 6 | G12C 4-21 or G12T 4-21 | YKLVVVGACGVGKSALTI or YKLVVVGATGVGKSALTI | 1778 | 18 18 |
| 7 | G13D 4-21 | YKLVVVGAGDVGKSALTI | 1790 | 18 |

A compound of the invention may be prepared from a mutant KRAS polypeptide, a linker precursor, and a lipid using methods known in the art. In some variations, a linker precursor is first linked to a lipid, e.g., as follows:

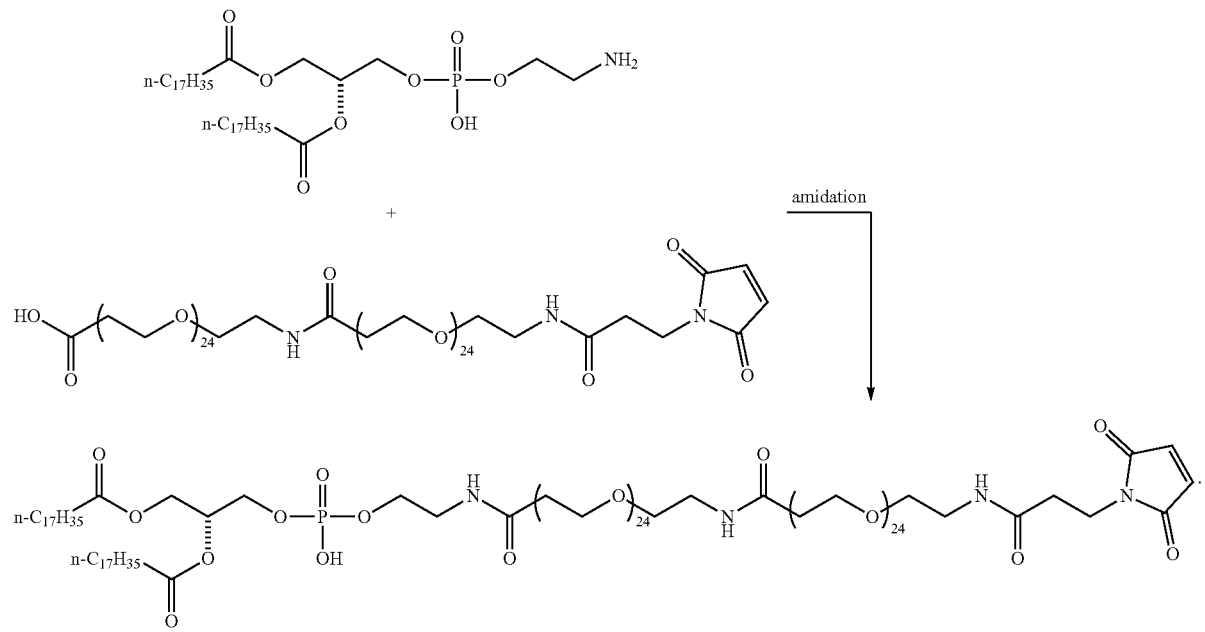

Amidation reaction conditions are known in the art, for example, typical amidation conditions include the use of reagents, such as EDC/DMAP, HATU/HOAt, or HBTU/HOAt. Alternatively, the carboxylate may be replaced with an O-succinimide ester, pentrafluorophenyl ester, or tetrafluorophenyl ester. The product of this reaction may then be reacted with a mutant KRAS polypeptide, e.g., as follows:

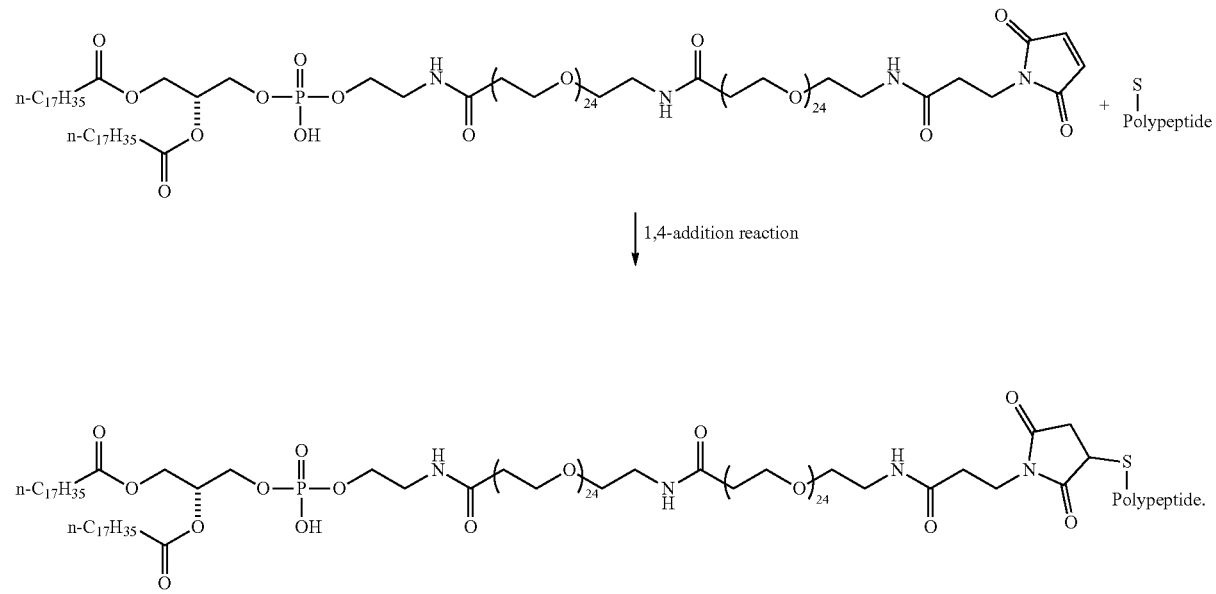

The 1,4-addition reaction may be carried out in an appropriate solvent, e.g., a polar organic solvent or water.

Alternatively, a compound of the invention may be prepared as follows. A linker precursor may be first linked to a lipid, e.g., as follows:

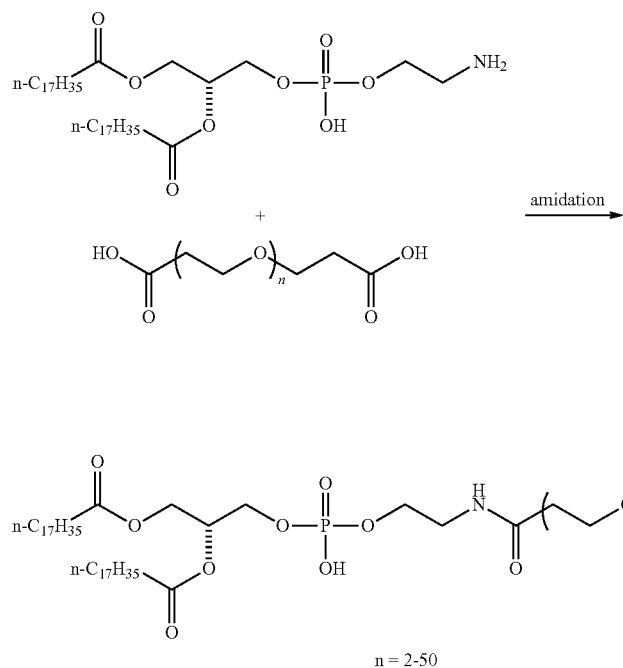

n = 2-50

The product may then be reacted with an amine group (e.g., N-terminal amine) in the mutant KRAS polypeptide to produce a compound of the invention:

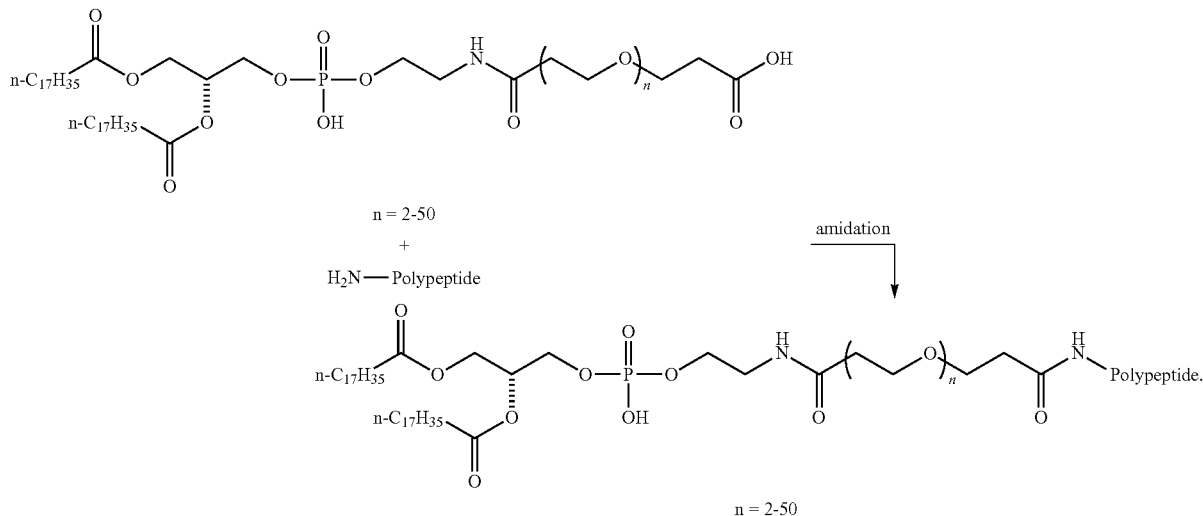

n = 2-50

A CpG oligonucleotide may be bonded directly or linked by a linker to the lipid. These compounds may be produced using the ordinary phosphoramidite chemistry known in the art. In some examples, the CpG oligonucleotide or CpG oligonucleotide that, at its 5' end, is bonded to GG may be reacted with the following compound:

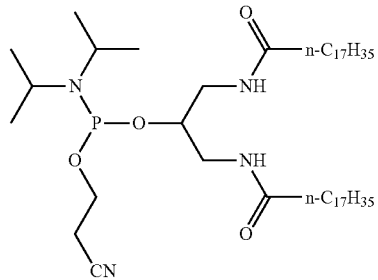

to produce an intermediate, which upon oxidation with (e.g., phosphite oxidation methods known in the art, e.g., a sulfurizing agent, such as 3-((N,N-dimethylaminomethyl-idene)amino)-3H-1,2,4-dithiazole-5-thione) and hydrolysis of the cyanoethyl group may produce a compound consisting of CpG oligonucleotide that, at its 5' end, is bonded or linked by a linker to the lipid:

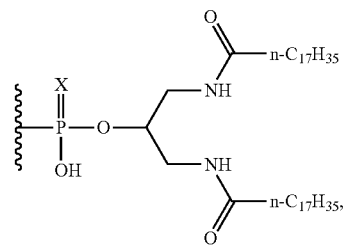

or a salt thereof, wherein X is O or S.

Dosing

The dose of each KRAS peptide administered can be in the range of 100 to 5000 μg per peptide (e.g., 700 μg/peptide, which would yield a peptide dose of 4900 μg for a group of 7 peptides).

If an adjuvant is administered with the KRAS peptide, the dose of the adjuvant can be, on a body weight basis, as high as 0.48 mg/kg. Exemplary dosing regimens are shown below in Table 3.

TABLE 3

Figure 6:
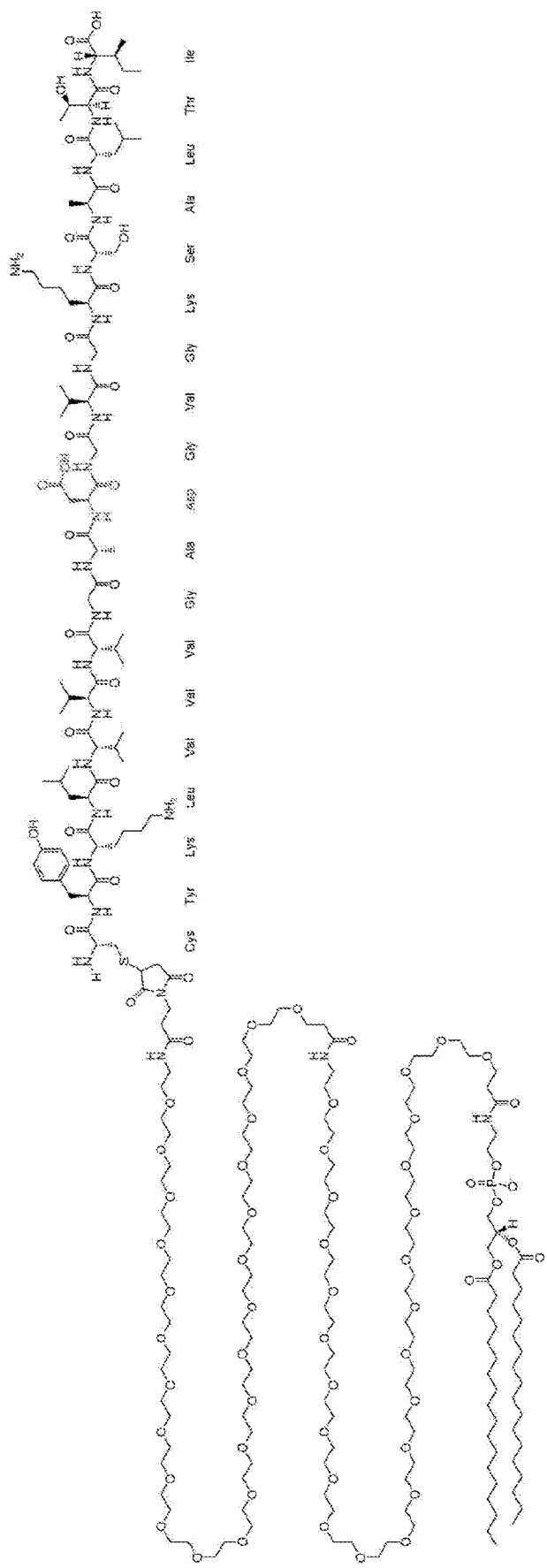
FIG. 6 shows the structure of the amphiphile-peptide G12D 4-21 (SEQ ID NO:1).
Figure 7:
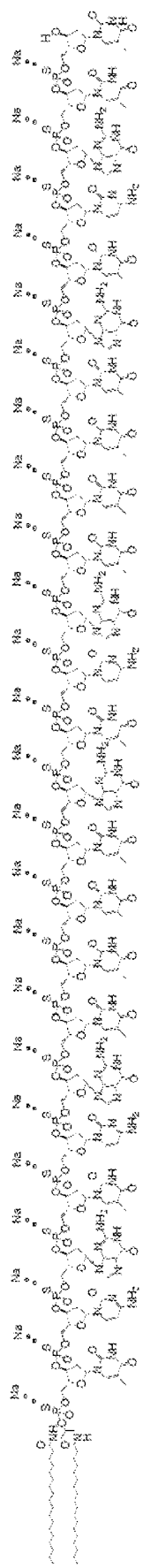
FIG. 7 shows the structure of amphiphile-CpG-7909. All sugars are deoxyribose. All internucleoside linkages are phosphorothioate. The structure is presented as the sodium salt.

| Dosing | Adjuvant (e.g. Amph-CpG-7909; FIG. 6) | Peptide |
| --- | --- | --- |
| Dose 1 (low) | 0.1 mg | 700 μg for each of 7 peptides |
| Dose 2 (medium) | 0.5 mg | 700 μg for each of 7 peptides |
| Dose 3 (high) | 2.5 mg | 700 μg for each of 7 peptides |

In order that this invention be more fully understood, the following examples are set forth. These examples are for the purpose of illustration only and are not to be construed as limiting the scope of the invention in any way.

EXAMPLES

Example 1: Amphiphile KRas G12D Elicits an Immune Response

The efficacy of soluble-KRas (KRas) or amphiphile-KRas (aKRas) (FIG. 6) mutant sequences and an amphiphile-CpG adjuvant (aCpG) to elicit an immune response was determined. In these experiments five-times as much aCpG as amphiphile-KRas was used because CpG escalation experiments suggested that this dose may be more efficacious.

The experimental design included the following 4 groups of C57BL16 mice immunized with the listed compounds (n=5 for each group):
1. KRas G12D+aCpG
2. aKRas G12D+aCpG
3. KRas G12D+pIC
4. No immunization PolyIC (pIC) was used as a benchmark adjuvant control.

The adjuvant, as well as peptide stock, solutions were dissolved in H₂O. Final injections were diluted with 1×PBS (phosphate buffered saline).

The aKRas peptides used were 18mer sequences of mutant sequences with a G12D substitution (amino acids 4-21 of wild-type→YKLVVVGAGGVGKSALTI (SEQ ID NO:9)). 20 µg in 100 µl were used for each injection.

The aCpG sequence used was the CpG1826 sequence (5'-tccatgacgttcctgacgtt-3'; SEQ ID NO:10) with two guanines added at the 5' end (5'-gg tccatgacgttcctgacgtt-3'; SEQ ID NO:11) at a concentration of 5 nmol for each 100 µl injection. CpG1826 is an optimal mouse sequence while CpG7909 is optimal for humans and poorly active in mice. CpG1826 and CpG7909 are in the same CpG class (class B) and generally have similar activity profiles in their respective species.

50 µg of pIC were used for each 100 µl injection.

Primer immunizations were given subcutaneously (s.c.) into the tail base (day 0) with one booster dose after 2 weeks (day 14). ELISpot analysis for IFNγ on splenocytes was performed, using standard protocols, 8 days after booster dose administration (day 21). Splenocytes (10⁶ cells/well) were activated with 5 µg/well of G12D sequence 18mer (aa4-21)→YKLVVVGADGVGKSALTI (SEQ ID NO:1). As shown in FIG. 1, aKRas in combination with aCpG activated splenocytes while soluble KRas in combination with aCpG, and the untreated and soluble KRas and pIC control groups, did not.

Example 2: Amphiphile KRas G12R and G12V Elicit an Immune Response

The efficacy of additional soluble-KRas (KRas) or amphiphile-KRas (aKRas) mutant sequences and an amphiphile-CpG adjuvant (aCpG) or soluble CpG (CpG) to elicit an immune response was determined.

The experimental design included the following 7 groups of C57BL/6 mice immunized with the listed compounds (n=5 for each group):
1. KRas G12R+CpG
2. KRas G12V+CpG
3. KRas G12R+pIC
4. KRas G12V+pIC
5. aKRas G12R+aCpG
6. aKRas G12V+aCpG
7. No immunization The adjuvant as well as peptide stock solutions are dissolved in H₂O. Final injections are diluted with 1×PBS.

The aKras peptides used were 18mer sequences of mutant sequences with G12R/V substitutions (SEQ amino acids 4-21 of wild-type→YKLWVGAGGVGKSALTI (SEQ ID NO:9)). 20 µg in 100 µl were used for each injection.

The aCpG sequence used was the CpG1826 sequence (5'-tccatgacgttcctgacgtt-3'; SEQ ID NO:10) with two guanines added at the 5' end (5'-gg tccatgacgttcctgacgtt-3'; SEQ ID NO:11) at a concentration of 5 nmol for each 100 µl injection.

50 µg of pIC were used for each 100 µl injection.

Primer immunizations were given subcutaneously (s.c.) into the tail base with one booster dose after 2 weeks (d14). ELISpot analysis for IFNγ on splenocytes was performed, using standard protocols, 7 days after booster dose administration (d21). Splenocytes (10⁶ cells/well) were activated with 5 µg/well of either: the G12V sequence 18mer (aa4-21)→YKLVVVGAVGVGKSALTI (SEQ ID NO:2) or the G12R sequence 18mer (aa4-21)→YKLVVVGARGVGKSALTI (SEQ ID NO:3).

Figure 2:
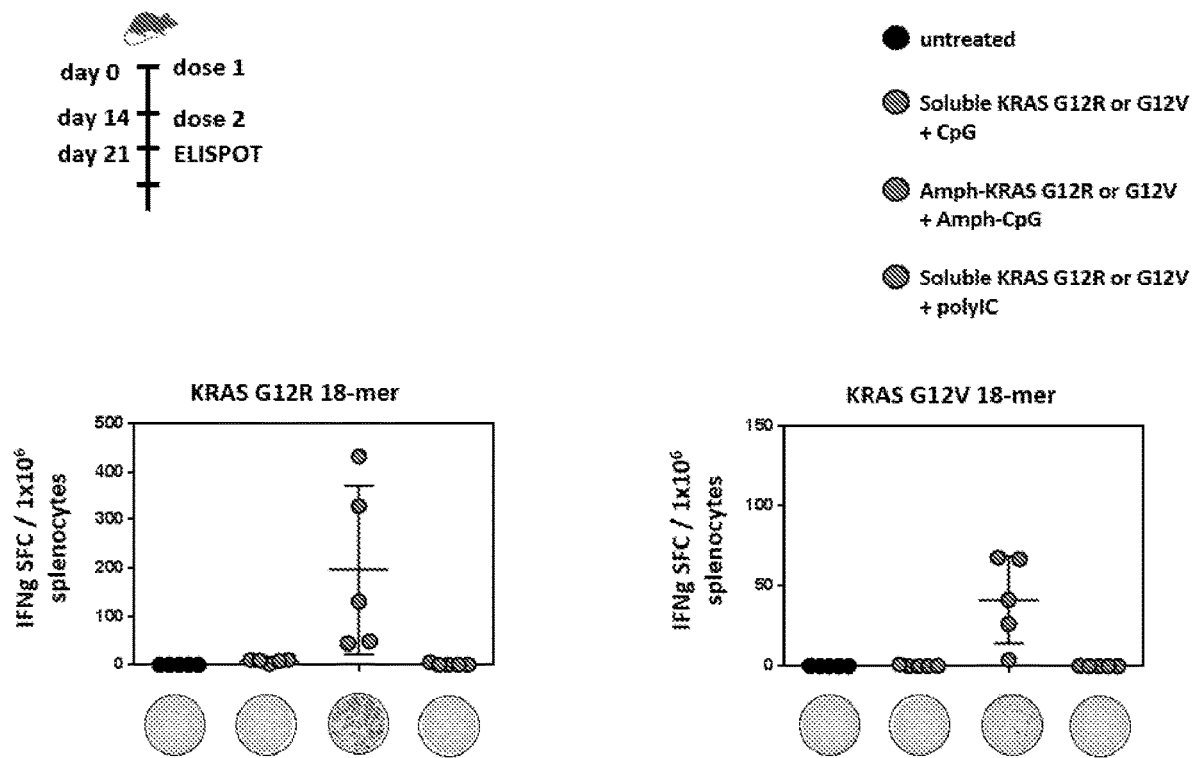
FIG. 2 shows that both aKRas G12R and G12V, in combination with aCpG, activated splenocytes, while neither soluble KRas G12R nor G12V in combination with aCpG, and the untreated and soluble KRas and pIC control groups, did not.

As shown in FIG. 2, both aKRas G12R and G12V in combination with aCpG activated splenocytes while neither soluble KRasG12R nor G12V in combination with aCpG, and the untreated and soluble KRas and pIC control groups, did not.

Example 3: Amphiphile KRas G12D Elicits a CD8⁺ T-Cell Immune Response

In wild-type B6 mice it is difficult to elicit a Kras-specific CD8⁺ T-cell response. B6 mice transgenic for the human HLA gene, A2.1, were immunized either with the soluble or amphiphile-conjugated forms of the KRas G12D antigen, as well as adjuvant (CpG or aCpG). The A2.1 allele is known to mount responses to the KRas peptides in humans.

The experimental design included the following 4 groups of B6 HLA-A2.1 Tg mice immunized with the listed compounds (n=5 for each group):
1. KRas wild-type+CpG
2. KRas 12D+CpG
3. aKRas 12D+aCpG
4. No immunization The adjuvant as well as peptide stock solutions were dissolved in H₂O. Final injections were diluted with 1×PBS.

The aKRas peptides used were 18mer sequences of mutant sequences with a G12D substitution (amino acids 4-21 of wild-type 4 YKLVVVGAGGVGKSALTI (SEQ ID NO:9)). 20 µg in 100 µl were used for each injection.

The aCpG sequence used was the CpG1826 sequence (5'-tccatgacgttcctgacgtt-3'; SEQ ID NO:10) with two guanines added at the 5' end (5'-gg tccatgacgttcctgacgtt-3'; SEQ ID NO:11) at a concentration of 5 nmol for each 100 µl injection.

The vaccine was administered subcutaneously to female mice bilaterally at the tail base at 50 µl per side. Two booster doses were given in two-week intervals.

Intracellular cytokine staining (ICS) analysis for IFNγ on peripheral blood mononuclear cells (PBMCs) and ELISpot analysis for IFNγ on splenocytes was performed, using standard protocols, 7 days after the second and third booster dose, respectively.

PBMCs/Splenocytes (10⁶ cells/well and 2×10⁶ cells/well) were activated with 5 µg/well of either SEQ ID NO:1 or one of SEQ ID NOS:12-20 as shown below:

```
1. 12D sequence 18mer (aa4-21) YKLVVVGADGVGKSALTI  (MHCII/CD4 epitope)

2. 12D sequence 17mer (aa5-21) KLVVVGADGVGKSALTI   (MHCII/CD4 epitope)

3. 12D sequence 10mer (aa5-14) KLVVVGADGV          (MHCI/CD8 epitope)

4. 12D sequence 9mer  (aa6-14) LVVVGADGV           (MHCI/CD8 epitope)
```

```
 5. 12D sequence 9mer  (aa7-15)  VVVGADGVG         (MHCI/CD8 epitope)

6. 12D sequence 9mer  (aa8-16)  VVGADGVGK         (MHCI/CD8 epitope)

7. 12D sequence 9mer  (aa9-17)  VGADGVGKS         (MHCI/CD8 epitope)

8. 12D sequence 9mer  (aa10-18) GADGVGKSA         (MHCI/CD8 epitope)

9. 12D sequence 9mer  (aa11-19) ADGVGKSAL         (MHCI/CD8 epitope)

10. 12D sequence 9mer  (aa12-20) DGVGKSALT         (MHCI/CD8 epitope)
```

Specific mutant peptides are given only to the mice that were immunized with the corresponding 18mer.

Figure 3:
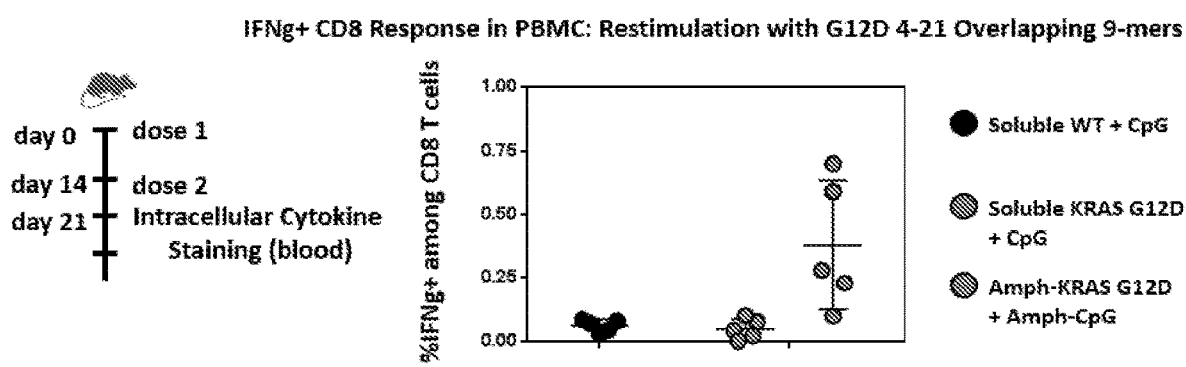
FIG. 3 shows a KRas-specific CD8$^+$ T-cell response for mice immunized with the combination of aKRas G12D and aCpG, but not for soluble KRas G12D in combination with CpG or soluble wild-type KRas in combination with CpG.

FIG. 3 shows a KRas-specific CD8' T-cell response for mice immunized with the combination of aKRas G12D and aCpG, but not for soluble KRas G12D in combination with CpG or soluble wild-type KRas in combination with CpG.

Example 4: Analysis for Higher Antigen Concentration and Different Dose Intervals The concentration of antigen was increased from 20 μg to 50 μg and bi-weekly (bw) or weekly (w) dose intervals were tested.

nines added at the 5' end (5'-gg tccatgacgttcctgacgtt-3'; SEQ ID NO:11) at a concentration of 5 nmol for each 100 μl injection.

Primer immunizations were given subcutaneously (s.c.) into the tail base with one booster dose after 2 weeks.

ELISpot analysis for IFNγ, and CBA (cytometric bead array) analysis for IL6, I-10, IL12, TNFα, IFNγ, and MCP1 was performed on splenocytes, using standard protocols, 7 days after booster dose administration. Splenocytes ($10^6$ cells/well) were activated with 5 μg/well of either SEQ ID NO:1 or one of SEQ ID NOS:12-21 as shown below:

```
 1. 12D sequence 18mer (aa4-21)  YKLVVVGADGVGKSALTI (MHCII/CD4 epitope)

2. 12D sequence 17mer (aa5-21)  KLVVVGADGVGKSALTI  (MHCII/CD4 epitope)

3. 12D sequence 10mer (aa5-14)  KLVVVGADGV         (MHCI/CD8 epitope)

4. 12D sequence 9mer  (aa5-13)  KLVVVGADG          (MHCI/CD8 epitope)

5. 12D sequence 9mer  (aa6-14)  LVVVGADGV          (MHCI/CD8 epitope)

6. 12D sequence 9mer  (aa7-15)  VVVGADGVG          (MHCI/CD8 epitope)

7. 12D sequence 9mer  (aa8-16)  VVGADGVGK          (MHCI/CD8 epitope)

8. 12D sequence 9mer  (aa9-17)  VGADGVGKS          (MHCI/CD8 epitope)

9. 12D sequence 9mer  (aa10-18) GADGVGKSA          (MHCI/CD8 epitope)

10. 12D sequence 9mer  (aa11-19) ADGVGKSAL          (MHCI/CD8 epitope)

11. 12D sequence 9mer  (aa12-20) DGVGKSALT          (MHCI/CD8 epitope)
```

The experimental design included the following 5 groups of C57BL/6 mice immunized with the listed compounds (n=5 for each group):

1. KRas 12D+CpG1826 (bw)
2. KRas 12D+CpG1826 (w)
3. aKRas 12D+aCpG1826 (bw)
4. aKRas 12D+aCpG1826 (w)
5. No immunization The adjuvant as well as peptide stock solutions were dissolved in H₂O. Final injections were diluted with 1×PBS.

The aKRas peptides used were 18mer sequences of mutant sequences with a G12D substitution (amino acids 4-21 of wild-type→YKLVVVGA$\underline{\text{D}}$GVGKSALTI (SEQ ID NO:9)). 50 μg in 100 μl were used for each injection.

The aCpG sequence used was the CpG1826 sequence (5'-tccatgacgttcctgacgtt-3'; SEQ ID NO:10) with two gua- Specific mutant peptides were given only to the mice that were immunized with the corresponding 18mer.

Separate plates were prepared for either short (9mer and 10mer) or long (17mer and 18mer) peptide stimulations. Cells from "No immunization" control mice were stimulated with all stimuli.

Figure 4:
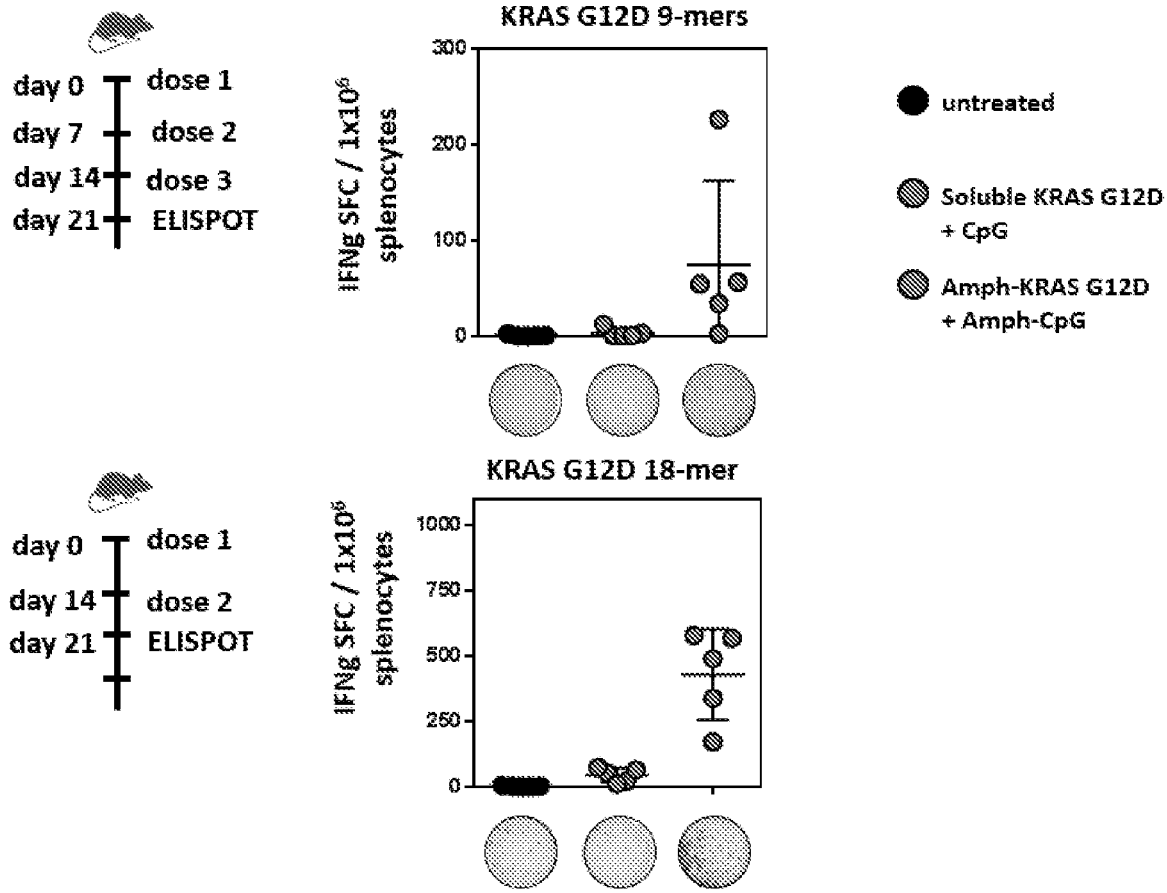
FIG. 4 shows a KRas-specific CD8$^+$ T-cell response (9mers) and CD8$^+$ or CD4$^+$ T-cell response (18mer) for mice immunized with the combination of aKRas G12D and aCpG, but not for soluble KRas G12D in combination with CpG or the untreated control.

FIG. 4 shows a KRas-specific CD8⁺ T-cell response (9mers) and CD8' or CD4*T-cell response (18mer) for mice immunized with the combination of aKRas G12D and aCpG, but not for soluble KRas G12D in combination with CpG or the untreated control.

Example 5: Further Analysis of KRAS Amphiphiles

Figure 5:
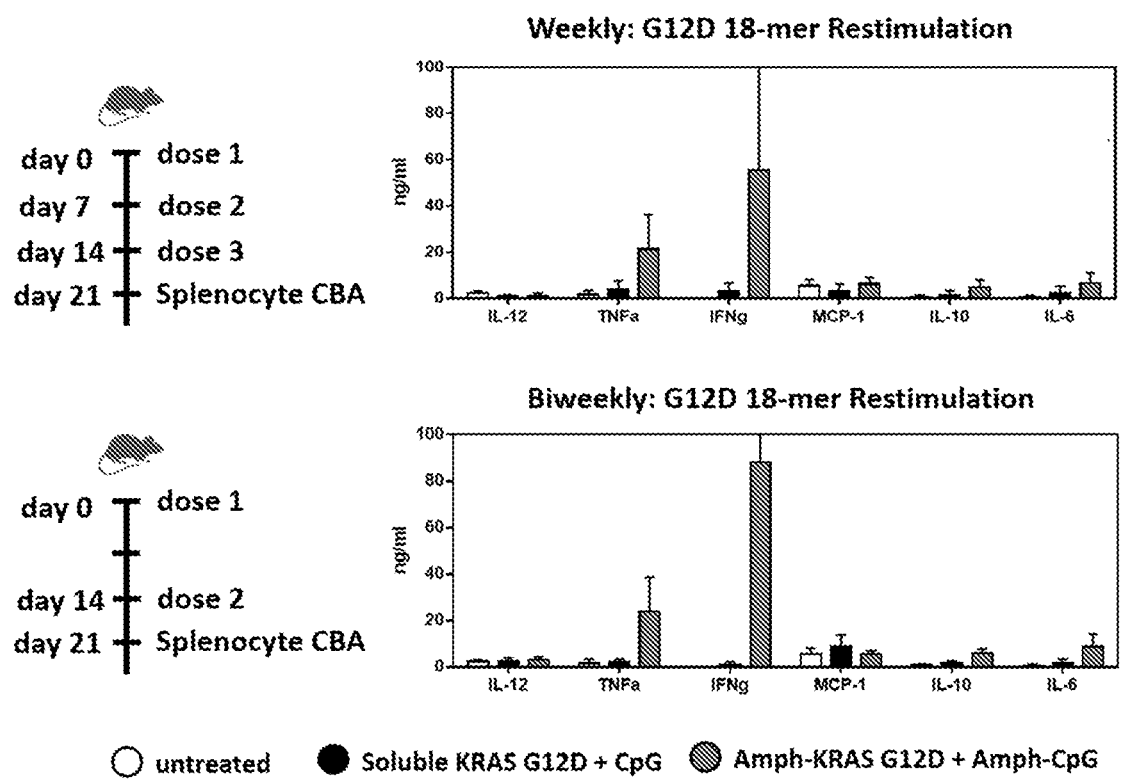
FIG. 5 shows amphiphile-KRas (Amph-KRAS) and amphipile-CpG (Amph-CpG) vaccines elicit superior endogenous T-cell responses compared to soluble KRas vaccines, as indicated by increased cytokine production by splenocytes in a cytokine bead array. Soluble KRAS G12D=YKLVVVGADGVGKSALTI (SEQ ID NO: 23); Amph-KRAS G12D=DSPE-amido-dPEG24-amido-dPEG24-CYKLVVVGADGVGKSALTI (SEQ ID NO: 1); KRAS G12D 18-mer=YKLVVVGADGVGKSALTI (SEQ ID NO:23); CBA=Cytokine bead array; IFN=interferon; IL=interleukin; KRAS=Kirsten Rat Sarcoma.

As described in the above Examples, the potential immunogenicity of a mutant KRAS peptide—amphiphile vaccine with aCpG adjuvant has been demonstrated in a C57BL/6 mouse model. These studies, and further studies, are summarized in the Table 4 and demonstrate that although mice historically mount poorer immunologic responses than humans to mutant KRAS peptides, due to species differences in MHC binding,
- subcutaneous administration of mutated KRAS Amph-Peptides (G12D (FIG. 6), G12R, and G12V) is effective at inducing KRAS-specific splenic T-cells in mice as identified by ELISPOT and cytokine bead array (FIG. 1, FIG. 2, FIG. 4, and FIG. 5)
- mutated KRAS Amph-Peptides (G12D, G12R, and G12V) combined with aCpG as the adjuvant are more effective at inducing KRAS-specific splenic T-cells than mutated KRAS peptides combined with either soluble CpG or polyinosinic:polycytidylic acid (poly IC) as the adjuvant (FIG. 1, FIG. 2, and FIG. 5) and
- mutated KRAS Amph-Peptides (G12D) combined with aCpG are more effective than soluble KRAS peptides combined with soluble CpG at eliciting both CD4 and CD8 T-cell responses as demonstrated through effector cytokine response upon restimulation with either long (18-mer) or minimal (9-mer) peptide epitopes (FIG. 4).

TABLE 4

| Test Article Doses/Dose Volume | ROA/Treatment Regimen | Results |
|---|---|---|
| 4 groups:<br>1) KRAS G12D + CpG;<br>2) Amph-KRAS G12D + aCpG;<br>3) KRAS G12D + Poly IC;<br>4) No Treatment<br>KRAS peptides (amphiphilic or soluble) were dosed at 20 µg; aCpG-1826 at 5 nmoL; and Poly IC at 50 µg; stock solutions were dissolved in water and final dose solutions in phosphate-buffered saline (PBS).<br>Dose volume: 100 µL administered divided as a SC injection on either side of the tail head (50 µL per injection site) | ROA: SC<br>Prime: Day 0<br>Boost: Day 14 | ELISPOT (IFNγ)<br>Results:<br>Amph-Peptide G12D + aCpG produced superior splenic T-cell responses when compared to either soluble G12D + soluble CpG or Poly IC |
| 7 groups:<br>1) KRAS G12R + CpG;<br>2) KRAS G12V + CpG<br>3) KRAS G12R + Poly IC;<br>4) KRAS G12V + Poly IC;<br>5) Amph-KRAS G12R + aCpG;<br>6) Amph-KRAS G12V + aCpG;<br>7) No Treatment<br>KRAS peptides (amphiphilic or soluble) were dosed at 20 µg; aCpG-1826 at 5 nmoL; and Poly IC at 50 µg; stock solutions were dissolved in water and final dose solutions in PBS.<br>Dose volume: 100 µL administered divided as a SC injection on either side of the tail head (50 µL per injection site) | ROA: SC<br>Prime: Day 0<br>Boost: Day 14 | ELISPOT (IFNγ)<br>Results:<br>KRAS peptide sequences are more immunogenic when conjugated to a lipid moiety than are soluble peptides |
| 5 groups:<br>1) KRAS G12D + CpG (bw);<br>2) KRAS G12D + CpG (w);<br>3) Amph-KRAS G12D + aCpG (bw);<br>4) Amph-KRAS G12D + aCpG (w);<br>5) No treatment<br>KRAS peptides (amphiphilic or soluble) were dosed at 50 µg; aCpG-1826 at 5 nmol; stock solutions were dissolved in water and final dose solutions in PBS.<br>Dose volume: 100 µL administered divided as a SC injection on either side of the tail head (50 µL per injection site) | ROA: SC<br>2 doses (prime + boost) were administered for the animals treated biweekly (bw) and 3 doses (prime + 2 boosts) were administered to the animals treated weekly (w):<br>Prime: Day 0 (w and bw)<br>Boost: Day 7 (w)<br>Boost: Day 14 (w and bw) | ELISPOT (IFNγ) and CBA Results:<br>Amphiphiles elicited endogenous CD8 and CD4 T-cell responses against mutant KRAS in C57BL/6 mice as assessed by both ELISPOT (IFNγ) and/or cytokine bead array (IFNγ, TNFα and IL-6) |

CBA = cytometric bead array;
ELISPOT = enzyme-linked immunospot;
IFNγ = interferon gamma;
IL-6 = interleukin 6;
KRAS = Kirsten Rat Sarcoma;
poly IC = polyinosinic:polycytidylic acid;
ROA = route of administration;
SC = subcutaneous;
TNFα = tumor necrosis factor alpha Other Embodiments While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Some embodiments of the invention are within the following numbered paragraphs.

1. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence comprises or consists of an amino acid sequence selected from the group consisting of YKLVVVGADGVGKSALTI (SEQ ID NO:23), YKLVVVGAVGVGKSALTI (SEQ ID NO:24), YKLVVVGARGVGKSALTI (SEQ ID NO:25), YKLVVVGAAGVGKSALTI (SEQ ID NO:26), YKLVVVGASGVGKSALTI (SEQ ID NO:27), YKLVVVGACGVGKSALTI (SEQ ID NO:28), YKLVVVGATGVGKSALTI (SEQ ID NO:29), and YKLVVVGAGDVGKSALTI (SEQ ID NO:30).

2. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence comprises or consists of an amino acid sequence selected from the group consisting of CYKLVVVGADGVGKSALTI (SEQ ID NO:1), CYKLWVGAVGVGKSALTI (SEQ ID NO:2), CYKLVVVGARGVGKSALTI (SEQ ID NO:3), CYKLWVGAAGVGKSALTI (SEQ ID NO:4), CYKLVVVGASGVGKSALTI (SEQ ID NO:5), CYKLWVGACGVGKSALTI (SEQ ID NO:6), CYKLVVVGATGVGKSALTI (SEQ ID NO:22), and CYKLWVGAGDVGKSALTI (SEQ ID NO:7).

3. The compound of paragraph 1 or 2, wherein the mutant KRAS sequence, at its N-terminus, is conjugated to the linker through a cysteine-maleimide linkage.

4. The compound of any one of paragraphs 1-3, wherein linker comprises 48 repeat units of polyethylene glycol.

5. The compound of paragraph 1 or 2, wherein the mutant KRAS sequence, at its N-terminus, is conjugated to the following structure:

6. A composition comprising one or more compounds of any one of paragraphs 1-5 and a pharmaceutically acceptable carrier.

7. The composition of paragraph 6, wherein the composition comprises (1) a compound comprising the amino acid sequence YKLVVVGADGVGKSALTI (SEQ ID NO:23), (2) a compound comprising the amino acid sequence YKLVVVGAVGVGKSALTI (SEQ ID NO:24), (3) a compound comprising the amino acid sequence YKLVVVGARGVGKSALTI (SEQ ID NO:25), (4) a compound comprising the amino acid sequence YKLVVVGAAGVGKSALTI (SEQ ID NO:26), (5) a compound comprising the amino acid sequence YKLWVGASGVGKSALTI (SEQ ID NO:27), (6) a compound comprising the amino acid sequence YKLWVGACGVGKSALTI (SEQ ID NO:28) or a compound comprising the amino acid sequence YKLVVVGATGVGKSALTI (SEQ ID NO:29), and (7) a compound comprising the amino acid sequence YKLWVGAGDVGKSALTI (SEQ ID NO:30).

8. The composition of paragraph 6, wherein the composition comprises (1) a compound comprising the amino acid sequence CYKLVVVGADGVGKSALTI (SEQ ID NO:1), (2) a compound comprising the amino acid sequence CYKLVVVGAVGVGKSALTI (SEQ ID NO:2), (3) a compound comprising the amino acid sequence CYKLWVGARGVGKSALTI (SEQ ID NO:3), (4) a compound comprising the amino acid sequence CYKLWVGAAGVGKSALTI (SEQ ID NO:4), (5) a compound comprising the amino acid sequence CYKLWVGASGVGKSALTI (SEQ ID NO:5), (6) a compound comprising the amino acid sequence CYKLVVVGACGVGKSALTI (SEQ ID NO:6) or a compound comprising the amino acid sequence CYKLVVVGATGVGKSALTI (SEQ ID NO:22), and (7) a compound comprising the amino acid sequence CYKLWVGAGDVGKSALTI (SEQ ID NO:7).

9. The composition of any one of paragraphs 6-8, wherein the composition further comprises a compound consisting of the nucleotide sequence 5'-TCGTCGTTTTGTCGTTTTGTCGTT-3' (SEQ ID NO:8), which, at its 5' end, is bonded or linked by a linker to the following lipid:

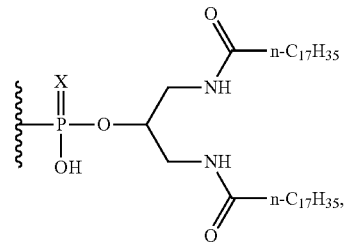

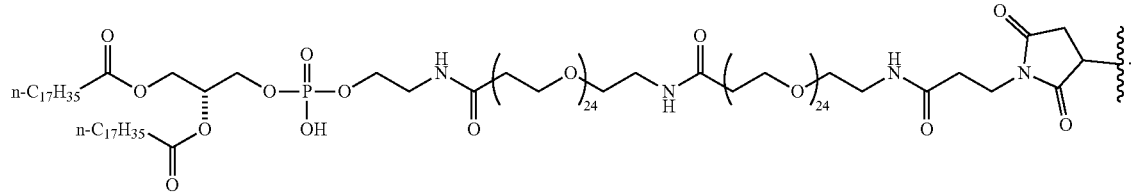

or a salt thereof,
wherein X is O or S.

10. The composition of paragraph 6, wherein the composition comprises 700 µg of each compound.

11. A method of treating a cancer in a human patient, the method comprising administering the composition of any one of paragraphs 6-10 to the patient.

12. The method of paragraph 11, wherein the method further comprises administering an adjuvant.

13. The method of paragraph 12, wherein the adjuvant comprises a CpG nucleotide sequence.

14. The method of paragraph 13, wherein the CpG nucleotide sequence comprises 5'-TCGTCGTTTTGTCGTTTTGTCGTT-3' (SEQ ID NO: 8).

15. The method of any one of paragraphs 12-14, wherein 0.1 mg, 0.5 mg, or 2.5 mg of the adjuvant is administered.

16. The method of paragraph 10, wherein the method further comprises administering to the patient a compound consisting of the nucleotide sequence 5'-TCGTCGTTTTGTCGTTTTGTCGTT-3' (SEQ ID NO:8), which, at its 5' end, is bonded or linked by a linker to the following lipid:

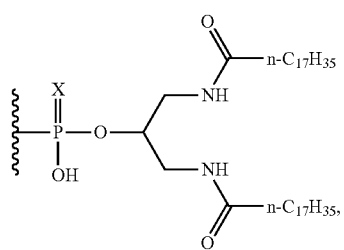

or a salt thereof,
wherein X is O or S.

17. The composition of paragraph 9 or the method of paragraph 16, wherein the nucleotide sequence is bonded to the lipid.

18. The method of paragraph 16 or 17, wherein 0.1 mg, 0.5 mg, or 2.5 mg of the compound consisting of the nucleotide sequence 5'-TCGTCGTTTTGTCGTTTTGTCGTT-3' (SEQ ID NO:8), which, at its 5' end, is bonded or linked by a linker to the following lipid:

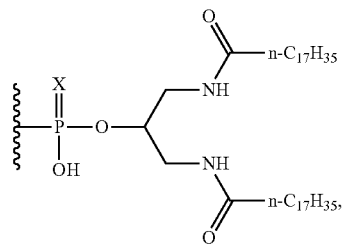

or a salt thereof,
wherein X is O or S,
is administered.

19. The method of any one of paragraphs 11-16 or 18, wherein the cancer is a pancreatic cancer, a lung cancer, or a colorectal cancer.

20. The method of any one of paragraphs 11-16 or 18, wherein all internucleoside groups connecting the nucleosides in 5'-TCGTCGTTTTGTCGTTTTGTCGTT-3' (SEQ ID NO:8) are phosphorothioates.

21. A kit comprising (i) a compound of any one of paragraphs 1-5, or a composition of any one of paragraphs 6-8, and (ii) a compound consisting of the nucleotide sequence 5'-TCGTCGTTTTGTCGTTTTGTCGTT-3' (SEQ ID NO:8), which, at its 5' end, is bonded or linked by a linker to the following lipid:

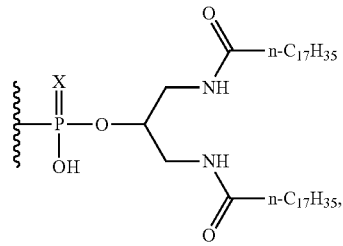

or a salt thereof,
wherein X is O or S.

Other embodiments are within the following claims.

---

What is claimed is:

1. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence consists of an amino acid sequence selected from the group consisting of CYKLVVVGAD-GVGKSALTI (SEQ ID NO:1), CYKLVVVGAVGVGK-SALTI (SEQ ID NO:2), CYKLVVVGARGVGKSALTI (SEQ ID NO:3), CYKLVVVGAAGVGKSALTI (SEQ ID NO:4), CYKLVVVGASGVGKSALTI (SEQ ID NO:5), CYKLVVVGACGVGKSALTI (SEQ ID NO:6), CYKLVVVGAGDVGKSALTI (SEQ ID NO:7), CYKLVVVGATGVGKSALTI (SEQ ID NO:22), YKLVVVGADGVGKSALTI (SEQ ID NO:23), YKLVVVGAVGVGKSALTI (SEQ ID NO:24), YKLVVVGARGVGKSALTI (SEQ ID NO:25), YKLVVVGAAGVGKSALTI (SEQ ID NO:26), YKLVVVGASGVGKSALTI (SEQ ID NO:27), YKLVVVGACGVGKSALTI (SEQ ID NO:28), YKLVVVGATGVGKSALTI (SEQ ID NO:29), and YKLVVVGAGDVGKSALTI (SEQ ID NO:30).

2. The compound of claim 1, wherein the mutant KRAS sequence selected from the group consisting of SEQ ID NOs: 1, 2, 3, 4, 5, 6, 7, and 22, at the N-terminus, is conjugated to the linker through a cysteine-maleimide linkage.

3. The compound of claim 1 or 2, wherein the linker comprises 48 repeat units of polyethylene glycol.

4. The compound of claim 1, wherein the mutant KRAS sequence, at the N-terminus, is conjugated to the following structure:

5. The compound of claim 1, wherein the linker comprises 2 to 50 repeat units of polyethylene glycol.

6. A kit comprising the compound of claim 1.

7. A composition comprising one or more compounds of claim 1, and a pharmaceutically acceptable carrier.

8. The composition of claim 6, wherein the composition comprises 700 μg of each compound.

9. A method of treating a cancer in a human patient, the method comprising administering the composition of claim 7 to the human patient.

10. The method of claim 9, wherein the method further comprises administering an adjuvant.

11. The method of claim 10, wherein the adjuvant comprises a CpG nucleotide sequence.

12. The method of claim 10, wherein 0.1 mg, 0.5 mg, or 2.5 mg of the adjuvant is administered.

13. The mthod of claim 9, wherein the cancer is a pancreatic cancer, a lung cancer, or a colorectal cancer.

14. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence consists of the amino acid sequence CYKLVVVGADGVGKSALTI (SEQ ID NO: 1), wherein the mutant KRAS sequence is conjugated to the linker through a cysteine-maleimide linkage.

15. The compound of claim 14, wherein the linker comprises 2 to 50 repeat units of polyethylene glycol.

16. The compound of claim 14, wherein the linker comprises 48 repeat units of polyethylene glycol.

17. A compound comprising a mutant KRAS sequence and a lipid, wherein the mutant KRAS sequence is conju-

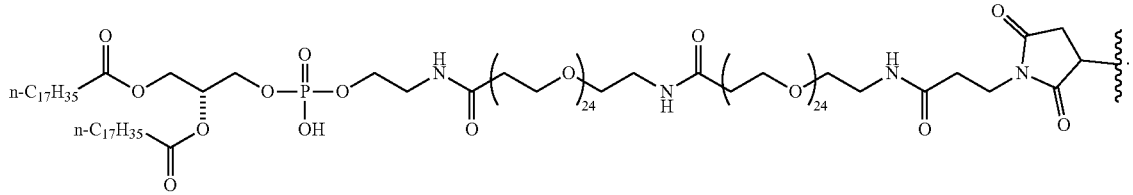

gated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence consists of the amino acid sequence CYKLVVVGAVGVGKSALTI (SEQ ID NO: 2), wherein the mutant KRAS sequence is conjugated to the linker through a cysteine-maleimide linkage.

18. The compound of claim 17, wherein the linker comprises 2 to 50 repeat units of polyethylene glycol.

19. The compound of claim 17, wherein the linker comprises 48 repeat units of polyethylene glycol.

20. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence consists of the amino acid sequence CYKLVVVGARGVGKSALTI (SEQ ID NO: 3), wherein the mutant KRAS sequence is conjugated to the linker through a cysteine-maleimide linkage.

21. The compound of claim 20, wherein the linker comprises 2 to 50 repeat units of polyethylene glycol.

22. The compound of claim 20, wherein the linker comprises 48 repeat units of polyethylene glycol.

23. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence consists of the amino acid sequence CYKLVVVGAAGVGKSALTI (SEQ ID NO: 4), wherein the mutant KRAS sequence is conjugated to the linker through a cysteine-maleimide linkage.

24. The compound of claim 23, wherein the linker comprises 2 to 50 repeat units of polyethylene glycol.

25. The compound of claim 23, wherein the linker comprises 48 repeat units of polyethylene glycol.

26. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence consists of the amino acid sequence CYKLVVVGASGVGKSALTI (SEQ ID NO: 5), wherein the mutant KRAS sequence is conjugated to the linker through a cysteine-maleimide linkage.

27. The compound of claim 26, wherein the linker comprises 2 to 50 repeat units of polyethylene glycol.

28. The compound of claim 26, wherein the linker comprises 48 repeat units of polyethylene glycol.

29. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence consists of the amino acid sequence CYKLVVVGAGDVGKSALTI (SEQ ID NO: 7), wherein the mutant KRAS sequence is conjugated to the linker through a cysteine-maleimide linkage.

30. The compound of claim 29, wherein the linker comprises 2 to 50 repeat units of polyethylene glycol.

31. The compound of claim 29, wherein the linker comprises 48 repeat units of polyethylene glycol.

32. A compound comprising a mutant KRAS sequence and a lipid, wherein the mutant KRAS sequence is conjugated to the lipid by a linker, and (i) the linker comprises one or more polyethylene glycol blocks, (ii) the lipid is 1,2-distearoyl-sn-glycero-3-phosphoethanolamine (DSPE), and (iii) the mutant KRAS sequence consists of the amino acid sequence YKLVVVGACGVGKSALTI (SEQ ID NO: 28), wherein the mutant KRAS sequence is conjugated to the linker through a cysteine-maleimide linkage.

33. The compound of claim 32, wherein the linker comprises 2 to 50 repeat units of polyethylene glycol.

34. The compound of claim 32, wherein the linker comprises 48 repeat units of polyethylene glycol.

\* \* \* \* \*

UNITED STATES PATENT AND TRADEMARK OFFICE
CERTIFICATE OF CORRECTION

PATENT NO. : 12,138,301 B2
APPLICATION NO. : 16/977155
DATED : November 12, 2024
INVENTOR(S) : Peter C. Demuth et al.

It is certified that error appears in the above-identified patent and that said Letters Patent is hereby corrected as shown below:

In the Claims

Column 35, Claim 3, Line 52, replace "1 or 2" with --1--.

Column 36, Claim 8, Line 29, replace "claim 6" with --claim 7--.

Column 36, Claim 13, Line 40, replace "mthod" with --method--.

Signed and Sealed this
Fifteenth Day of April, 2025

Coke Morgan Stewart
*Acting Director of the United States Patent and Trademark Office*

SEQUENCE LISTING

<160> NUMBER OF SEQ ID NOS: 31

<210> SEQ ID NO 1
<211> LENGTH: 19
<212> TYPE: PRT
<213> ORGANISM: Artificial Sequence
<220> FEATURE:
<223> OTHER INFORMATION: Synthetic Construct

<400> SEQUENCE: 1

Cys Tyr Lys Leu Val Val Val Gly Ala Asp Gly Val Gly Lys Ser Ala
1               5                   10                  15

Leu Thr Ile

<210> SEQ ID NO 2
<211> LENGTH: 19
<212> TYPE: PRT

```
<213> ORGANISM: Artificial Sequence
<220> FEATURE:
<223> OTHER INFORMATION: Synthetic Construct

<400> SEQUENCE: 2

Cys Tyr Lys Leu Val Val Val Gly Ala Val Gly Val Gly Lys Ser Ala
1               5                   10                  15

Leu Thr Ile

<210> SEQ ID NO 3
<211> LENGTH: 19
<212> TYPE: PRT
<213> ORGANISM: Artificial Sequence
<220> FEATURE:
<223> OTHER INFORMATION: Synthetic Construct

<400> SEQUENCE: 3

Cys Tyr Lys Leu Val Val Val Gly Ala Arg Gly Val Gly Lys Ser Ala
1               5                   10                  15

Leu Thr Ile

<210> SEQ ID NO 4
<211> LENGTH: 19
<212> TYPE: PRT
<213> ORGANISM: Artificial Sequence
<220> FEATURE:
<223> OTHER INFORMATION: Synthetic Construct

<400> SEQUENCE: 4

Cys Tyr Lys Leu Val Val Val Gly Ala Ala Gly Val Gly Lys Ser Ala
1               5                   10                  15

Leu Thr Ile

<210> SEQ ID NO 5
<211> LENGTH: 19
<212> TYPE: PRT
<213> ORGANISM: Artificial Sequence
<220> FEATURE:
<223> OTHER INFORMATION: Synthetic Construct

<400> SEQUENCE: 5

Cys Tyr Lys Leu Val Val Val Gly Ala Ser Gly Val Gly Lys Ser Ala
1               5                   10                  15

Leu Thr Ile

<210> SEQ ID NO 6
<211> LENGTH: 19
<212> TYPE: PRT
<213> ORGANISM: Artificial Sequence
<220> FEATURE:
<223> OTHER INFORMATION: Synthetic Construct

<400> SEQUENCE: 6

Cys Tyr Lys Leu Val Val Val Gly Ala Cys Gly Val Gly Lys Ser Ala
1               5                   10                  15

Leu Thr Ile

<210> SEQ ID NO 7
<211> LENGTH: 19
<212> TYPE: PRT
<213> ORGANISM: Artificial Sequence
<220> FEATURE:
<223> OTHER INFORMATION: Synthetic Construct
```

-continued

<400> SEQUENCE: 7

Cys Tyr Lys Leu Val Val Val Gly Ala Gly Asp Val Gly Lys Ser Ala
1               5                   10                  15

Leu Thr Ile

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
tcgtcgtttt gtcgttttgt cgtt                                          24

<210> SEQ ID NO 9
<211> LENGTH: 18
<212> TYPE: PRT
<213> ORGANISM: Artificial Sequence
<220> FEATURE:
<223> OTHER INFORMATION: Synthetic Construct

<400> SEQUENCE: 9

Tyr Lys Leu Val Val Val Gly Ala Gly Gly Val Gly Lys Ser Ala Leu
1               5                   10                  15

Thr Ile

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tccatgacgt tcctgacgtt                                               20

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct

<400> SEQUENCE: 11
ggtccatgac gttcctgacg tt                                            22

<210> SEQ ID NO 12
<211> LENGTH: 18
<212> TYPE: PRT
<213> ORGANISM: Artificial Sequence
<220> FEATURE:
<223> OTHER INFORMATION: Synthetic Construct

<400> SEQUENCE: 12

Tyr Lys Leu Val Val Val Gly Ala Asp Gly Val Gly Lys Ser Ala Leu
1               5                   10                  15

Thr Ile

<210> SEQ ID NO 13
<211> LENGTH: 17
<212> TYPE: PRT
<213> ORGANISM: Artificial Sequence
<220> FEATURE:

```
<223> OTHER INFORMATION: Synthetic Construct

<400> SEQUENCE: 13

Lys Leu Val Val Val Gly Ala Asp Gly Val Gly Lys Ser Ala Leu Thr
1               5                   10                  15
Ile

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Lys Leu Val Val Val Gly Ala Asp Gly Val
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Leu Val Val Val Gly Ala Asp Gly Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Val Val Val Gly Ala Asp Gly Val Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Val Val Gly Ala Asp Gly Val Gly Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Val Gly Ala Asp Gly Val Gly Lys Ser
1               5

<210> SEQ ID NO 19
<211> LENGTH: 9
<212> TYPE: PRT
<213> ORGANISM: Artificial Sequence
```

<220> FEATURE:
<223> OTHER INFORMATION: Synthetic Construct

<400> SEQUENCE: 19

Gly Ala Asp Gly Val Gly Lys Ser Ala
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Ala Asp Gly Val Gly Lys Ser Ala Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Asp Gly Val Gly Lys Ser Ala Leu Thr
1               5

<210> SEQ ID NO 22
<211> LENGTH: 19
<212> TYPE: PRT
<213> ORGANISM: Artificial Sequence
<220> FEATURE:
<223> OTHER INFORMATION: Synthetic Construct

<400> SEQUENCE: 22

Cys Tyr Lys Leu Val Val Val Gly Ala Thr Gly Val Gly Lys Ser Ala
1               5                   10                  15

Leu Thr Ile

<210> SEQ ID NO 23
<211> LENGTH: 18
<212> TYPE: PRT
<213> ORGANISM: Artificial Sequence
<220> FEATURE:
<223> OTHER INFORMATION: Synthetic Construct

<400> SEQUENCE: 23

Tyr Lys Leu Val Val Val Gly Ala Asp Gly Val Gly Lys Ser Ala Leu
1               5                   10                  15

Thr Ile

<210> SEQ ID NO 24
<211> LENGTH: 18
<212> TYPE: PRT
<213> ORGANISM: Artificial Sequence
<220> FEATURE:
<223> OTHER INFORMATION: Synthetic Construct

<400> SEQUENCE: 24

Tyr Lys Leu Val Val Val Gly Ala Val Gly Val Gly Lys Ser Ala Leu
1               5                   10                  15

Thr Ile

```
<210> SEQ ID NO 25
<211> LENGTH: 18
<212> TYPE: PRT
<213> ORGANISM: Artificial Sequence
<220> FEATURE:
<223> OTHER INFORMATION: Synthetic Construct

<400> SEQUENCE: 25

Tyr Lys Leu Val Val Val Gly Ala Arg Gly Val Gly Lys Ser Ala Leu
1               5                   10                  15

Thr Ile

<210> SEQ ID NO 26
<211> LENGTH: 18
<212> TYPE: PRT
<213> ORGANISM: Artificial Sequence
<220> FEATURE:
<223> OTHER INFORMATION: Synthetic Construct

<400> SEQUENCE: 26

Tyr Lys Leu Val Val Val Gly Ala Ala Gly Val Gly Lys Ser Ala Leu
1               5                   10                  15

Thr Ile

<210> SEQ ID NO 27
<211> LENGTH: 18
<212> TYPE: PRT
<213> ORGANISM: Artificial Sequence
<220> FEATURE:
<223> OTHER INFORMATION: Synthetic Construct

<400> SEQUENCE: 27

Tyr Lys Leu Val Val Val Gly Ala Ser Gly Val Gly Lys Ser Ala Leu
1               5                   10                  15

Thr Ile

<210> SEQ ID NO 28
<211> LENGTH: 18
<212> TYPE: PRT
<213> ORGANISM: Artificial Sequence
<220> FEATURE:
<223> OTHER INFORMATION: Synthetic Construct

<400> SEQUENCE: 28

Tyr Lys Leu Val Val Val Gly Ala Cys Gly Val Gly Lys Ser Ala Leu
1               5                   10                  15

Thr Ile

<210> SEQ ID NO 29
<211> LENGTH: 18
<212> TYPE: PRT
<213> ORGANISM: Artificial Sequence
<220> FEATURE:
<223> OTHER INFORMATION: Synthetic Construct

<400> SEQUENCE: 29

Tyr Lys Leu Val Val Val Gly Ala Thr Gly Val Gly Lys Ser Ala Leu
1               5                   10                  15

Thr Ile

<210> SEQ ID NO 30
<211> LENGTH: 18
<212> TYPE: PRT
```

```
-continued

<213> ORGANISM: Artificial Sequence
<220> FEATURE:
<223> OTHER INFORMATION: Synthetic Construct

<400> SEQUENCE: 30

Tyr Lys Leu Val Val Val Gly Ala Gly Asp Val Gly Lys Ser Ala Leu
1               5                   10                  15

Thr Ile

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Lys Leu Val Val Val Gly Ala Asp Gly
1               5
```